United States Patent
DeFrancesco et al.

(10) Patent No.: US 11,085,939 B2
(45) Date of Patent: Aug. 10, 2021

(54) QUANTIFYING PHOSPHATIDYLETHANOL FROM BLOOD SAMPLES

(71) Applicant: LOYOLA UNIVERSITY OF CHICAGO, Chicago, IL (US)

(72) Inventors: James Vincent DeFrancesco, Arlington Heights, IL (US); Majid Afshar, Chicago, IL (US)

(73) Assignee: LOYOLA UNIVERSITY OF CHICAGO, Chicago, IL (US)

(*) Notice: Subject to any disclaimer, the term of this patent is extended or adjusted under 35 U.S.C. 154(b) by 268 days.

(21) Appl. No.: 16/361,758

(22) Filed: Mar. 22, 2019

(65) Prior Publication Data

US 2019/0293668 A1 Sep. 26, 2019

Related U.S. Application Data

(60) Provisional application No. 62/646,770, filed on Mar. 22, 2018.

(51) Int. Cl.
*G01N 33/98* (2006.01)
*G01N 33/68* (2006.01)
*G01N 1/40* (2006.01)
*G01N 30/72* (2006.01)
*G01N 30/02* (2006.01)

(52) U.S. Cl.
CPC .......... *G01N 33/98* (2013.01); *G01N 1/4055* (2013.01); *G01N 30/7206* (2013.01); *G01N 33/6848* (2013.01); *G01N 2001/4061* (2013.01); *G01N 2030/025* (2013.01)

(58) Field of Classification Search
CPC .. G01N 33/98; G01N 33/6848; G01N 1/4055; G01N 30/7206; G01N 2001/4061; G01N 2030/025; G01N 33/92
See application file for complete search history.

(56) References Cited

PUBLICATIONS

Isaksson et al., "Posphatidylethanol in blood (B-PEth): A marker for alcohol use and abuse," Mar. 25, 2011, Drug Testing and Analysis, vol. 3, pp. 195-200. (Year: 2011).*
Afshar et al., Cut-Point Levels of Phosphatidylethanol to Identify Alcohol Misuse in a Mixed Cohort Including Critically Ill Patients, Alcohol Clin. Exp. Res., 41(10):1745-53 (Oct. 2017).
Hahn et al., The formation, elimination, interpretation, and future research needs of phosphatidylethanol for research studies and clinical practice, Alcohol Clin. Exp. Res., 40:2292-5 (2016).
Isaksson et al., Phosphatidylethanol in blood (B-PEth): a marker for alcohol use and abuse, Drug Test Anal., 3(4):195-200 (Apr. 2011).
Lowery et al., Use of alcohol biomarkers to identify alcohol misuse in organ donors, Alcohol, 73:67-72 (Dec. 2018).

(Continued)

*Primary Examiner* — Samuel P Siefke
*Assistant Examiner* — Michael Paul Shimek
(74) *Attorney, Agent, or Firm* — Marshall, Gerstein & Borun LLP

(57) ABSTRACT

Disclosed herein is a method for quantifying phosphatidylethanol ("PEth"), a direct ethanol biomarker, from a blood sample using gas chromatography mass spectrometry. The method disclosed herein is useful for diagnosing acute and chronic alcohol abuse.

22 Claims, 4 Drawing Sheets

(56) References Cited

PUBLICATIONS

Mokdad et al., Actual causes of death in the United States, 2000, JAMA, 291(10):1238-45 (Mar. 2004).

Wurst et al., Ethanol metabolites: Their role in the assessment of alcohol intake, Alcohol. Clin. Exp. Res., 39(11):2060-72 (Nov. 2015).

Yon et al., Analysis of trimethylsilyl derivatization products of phosphatidylethanol by gas chromatography-mass spectrometry, Exp. Mol. Med., 32(4):243-5 (Dec. 2000).

* cited by examiner

QUANTIFYING PHOSPHATIDYLETHANOL FROM BLOOD SAMPLES

CROSS REFERENCE TO RELATED APPLICATION

This application claims priority to U.S. Provisional Patent Application No. 62/646,770, filed Mar. 22, 2018, the disclosure of which is hereby incorporated by reference in its entirety.

BACKGROUND

Technical Field

The present disclosure relates a method for quantifying phosphatidylethanol ("PEth) in a blood sample via gas chromatography mass spectrometry.

Description of Related Technology

Alcohol misuse, which includes both acute (e.g., binge) and chronic heavy daily use, accounts for 88,000 deaths every year, making it the fourth leading preventable cause of death in the United States, and the 12$^{th}$ leading cause of death overall. See, e.g., Mokdad et al., JAMA. 291(10): 1238-1245 (2004). Alcohol biomarkers are routinely used in the clinical setting to screen for alcohol misuse, including blood alcohol content ("BAC"), gamma-glutamyltransferase ("GGT"), aspartate aminotransferase ("AST"), alanine amino transferase ("ALT"), and mean corpuscular volume ("MCV"). Within 24 hours of consumption, ethanol in the molecular form can be detected in blood and breath (prior to metabolism). Once the body's enzymes begin processing ethanol, its molecular structure is changed depending on the type of enzyme and stage of metabolism (Phase I or Phase II). In Phase II metabolism, ethanol is combined with other substances in the body and converted into direct biomarkers such as ethyl glucuronide ("EtG"), ethyl sulfate (EtS), fatty acid ethyl esters, and phosphatidylethanol ("PEth"). These direct biomarkers can be measured in numerous biological samples including blood, urine, hair, and nails.

PEth refers to a mixture of phospholipids that are formed in the presence of ethanol via the action of phospholipase D, and have the general structure:

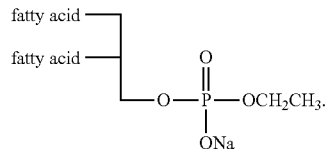

PEth has a half-life of approximately 4 to 10 days in blood, with detection windows of up to three weeks in heavy daily consumers. Therefore, PEth is considered a long-term, direct biomarker of ethanol that is correlated with excessive alcohol consumption.

Current methods of PEth quantitation in blood samples rely on direct detection of a single PEth species (16:0/18:1, shown below):

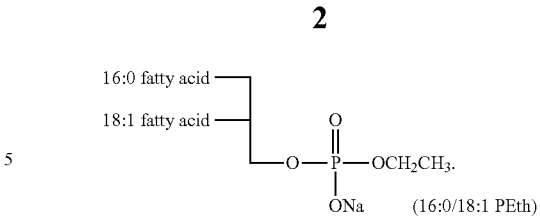

by liquid chromatography/mass spectrometry ("LC-MS") or liquid chromatography tandem mass spectrometry LC-MS/MS. Because, the current LC-MS methods measure only one of the many (over 40) PEth homologs, representing only 35-40% of all PEth contained in the red blood cells ("RBCs"), they have sub-optimal sensitivity. Moreover, the traditional methods are unable to detect decomposed PEth (e.g., through olefin oxidation, fatty acid hydrolysis, or glyceryl residue hydrolysis), rendering them ineffective in diagnosing chronic alcohol abuse or for detecting PEth in postmortem samples.

Thus, there is a need for methods of detecting PEth in a blood sample that have increased sensitivity and are unaffected by PEth decomposition.

SUMMARY

Provided herein is a method for quantifying phosphatidylethanol ("PEth") in a blood sample. The method includes extracting PEth from the blood sample by contacting the blood sample with a solvent comprising one or more of chloroform and an alcohol having 1-4 carbon atoms to form a PEth extract, concentrating the PEth extract to form a PEth concentrate, derivatizing the PEth in the PEth concentrate with a derivatizing agent to form a single PEth derivative having a structure of Formula (I):

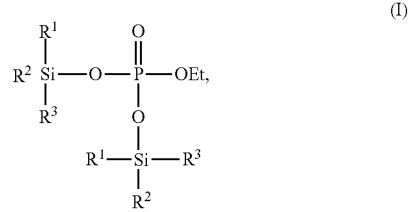

wherein each $R^1$, each $R^2$, and each $R^3$ independently is $C_{1-4}$alkyl, and quantifying the amount PEth derivative in the concentrate by gas chromatography mass spectrometry ("GC-MS"). In some embodiments, the blood sample comprises intact PEth and/or decomposed PEth. In some embodiments, the blood sample is a dried blood sample. In some embodiments, the blood sample is a whole blood sample. In some embodiments, each $R^1$, each $R^2$, and each $R^3$ independently is methyl or tert-butyl. In various embodiments, each $R^1$, $R^2$, and $R^3$ is methyl. In some cases, each $R^1$ and $R^2$ is methyl and each $R^3$ is tert-butyl. In some embodiments, the single PEth derivative is selected from the group consisting of:

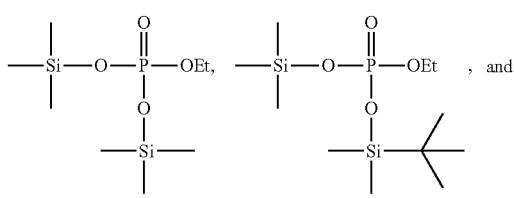

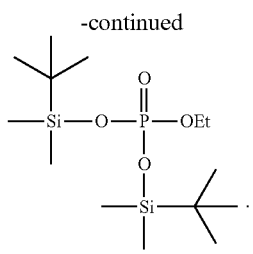

In some embodiments, the extraction solvent comprises chloroform and alcohol in a ratio of 90:10 to 70:30 by volume. In some cases, the extraction solvent comprises chloroform and alcohol in a ratio of 80:20 by volume. The alcohol can include one or more of methanol, ethanol, n-propanol, isopropyl alcohol, n-butanol, sec-butanol, isobutanol, and tert-butanol. In some embodiments, the alcohol comprises methanol or isopropyl alcohol. In various embodiments, the extracting comprises mixing or sonicating the blood sample with the solvent. In some cases, the concentrating comprises heating the extract, such as to a temperature of 35 to 45° C. In various cases, the derivatizing occurs in a derivatizing solvent comprising one or more of chloroform, acetonitrile, methylene chloride, toluene, and xylene. In some embodiments, the derivatizing agent is a silylating agent. The silylating agent can include one or more of N,O-Bis(trimethylsilyl)trifluoroacetamide ("BSTFA"), trimethylchlorosilane ("TMCS"), N-tert-Butyldimethylsilyl-N-methyltrifluoroacetamide ("MTBSTFA"), tert-Butyldimethylchlorosilane ("MTBCS"), N,O-Bis(trimethylsilyl)acetamide ("BSA"), Hexamethyldisilazane ("HMDS"), N-t-Butyldimethylsilylimidazole ("TBDMSIM"), N-Trimethylsilylimidazole ("TMSI"), N-Methyl-N-(trimethylsilyl)acetamide ("MSA"), N-(trimethylsilyl)dimethylamine ("TMSDMA"), N-trimethylsilyl-N-methyl trifluoroacetamide ("MSTFA"), and N,N-Diethyltrimethylsilylamine ("TMSDEA"). In some cases, the silylating agent comprises (i) a mixture of BSTFA and TMCS, (ii) a mixture of MTBSTFA and MTBCS, (iii) a mixture of MSTDA and TMCS, or (iv) MSTFA. In some embodiments, the silylating agent comprises a mixture of BSTFA and TMCS in a ratio of 99:1 by volume. In various cases, the derivatizing occurs at a temperature of 40 to 60° C. In some embodiments, the PEth extract is washed. In some embodiments, the PEth concentrate is filtered. In various embodiments, the PEth concentrate can be filtered under positive pressure through silica gel or alumina. In some embodiments, an internal standard can be added to the PEth concentrate. In some cases, the internal standard comprises one or more of a phosphatidyl alcohol, a deuterated phosphatidyl alcohol, and a long chain fatty acid. In some embodiments, the internal standard is phosphatidylmethanol ("PMeth"), phosphatidylbutanol ("PBut"), phosphatidylethanol-d5 or combinations thereof.

In some embodiments, the GC-MS can use electron impact ("EI") ionization. In embodiments, the GC-MS comprises a nonpolar phase column, a low-polarity phase column, or a mid-polarity phase column. In some embodiments, the column comprises dimethlpolysiloxane diphenyl, 1,4-bis(dimethylsiloxy)phenylene dimethylpolysiloxane, or a combination thereof. In some cases, the column comprises 100% dimethylpolysiloxane, 5%-diphenyl-95%-dimethylpolysiloxane, 50%-diphenyl-50%-dimethylpolysiloxane, 1,4-bis(dimethylsiloxy)phenylene dimethylpolysiloxane, or combinations thereof. In various embodiments, the column comprises 5%-diphenyl-95%-dimethylpolysiloxane. In some cases, the column further comprises an unphased guard column. In some embodiments, the GC-MS comprises an injector in splitless mode. In some cases, the quantifying comprises injecting about 0.100 ng/µL to about 6.00 ng/µL of the PEth derivative in chloroform into the GC-MS at an initial temperature of about 55 to about 75° C. or about 55 to about 100° C. held for about 1 to 10 minutes, flowing the PEth derivative through the GC-MS at a rate of about 1.0 mL to about 2.0 mL per minute, ramping the initial temperature to an interim temperature of about 125 to about 175° C. at a rate of about 3 to 7° C. per minute, and ramping the interim temperature to a final temperature of about 250 to about 350° C. at a rate of about 30 to 50° C. per minute. In various cases, the quantifying comprises injecting about 0.133 ng/µL to 5.330 ng/µL of the PEth derivative in chloroform into the GC-MS at an initial temperature of about 70° C. held for about 3 minutes, flowing the PEth derivative through the GC-MS at a rate of about 1.6 mL per minute, ramping the initial temperature to an interim temperature of about 150° C. at a rate of about 5° C. per minute, ramping the interim temperature to a final temperature of about 280° C. at a rate of about 40° C. per minute, and holding the final temperature for about 5 minutes.

Other features and advantages of the invention will be apparent from the following detailed description, and from the claims.

Figure 1:
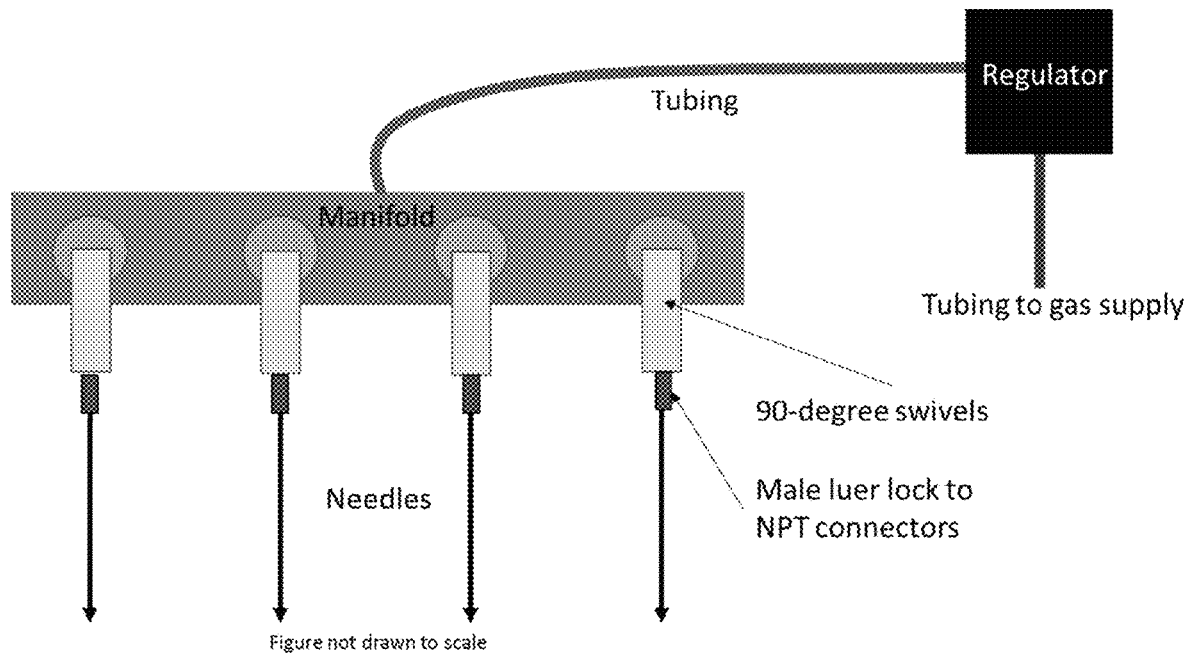
FIG. 1 depicts an embodiment of an evaporation apparatus used to concentrate the PEth extract. The evaporation apparatus includes a four outlet manifold that allows up to four samples to be dried simultaneously. The manifold is expandable with respect to the addition of outputs and linking of manifolds in series to accommodate the evaporation of more samples. Ninety-degree swivel adapters are attached to the manifold outlet ports to direct the gas stream in a downward direction. National pipe thread ("NPT") adapters are attached to each ninety-degree swivel adapter and terminate in luer lock fittings. Four-inch, 16 gauge dispensing needles are connected to each NPT adapter by luer lock. This configuration allows for a narrow gas stream to be directed into test tubes, vials, or similar vessels. All threaded connections are one quarter inch NPT. The back of the manifold is fitted with a barbed hose adapter connected to tubing. This tubing is connected to a regulator for control of gas flow and the regulator is connected to a gas supply. The entire manifold setup is mounted on a ring stand by a clamp to allow for facile vertical repositioning.

Further aspects and advantages will be apparent to those of ordinary skill in the art from a review of the following detailed description. While the methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION

Provided herein are methods for quantifying phosphatidylethanol ("PEth") in a blood sample using gas chromatography mass spectrometry ("GC-MS"). Unlike traditional methods for detecting PEth in a blood sample, the methods disclosed herein can detect PEth that has been decomposed, resulting in improved reliability over time, and allowing PEth quantification in chronic alcohol abusers and in postmortem samples. Because the methods disclosed herein can detect all or substantially all of PEth homologs present in a blood sample, not just one specific homolog, the methods exhibit increased sensitivity over the traditional methods. Furthermore, the methods disclosed herein are advantageous over traditional methods of PEth detection because they provide more reproducible or consistent results in a more timely manner for real-time bedside care.

The methods disclosed herein comprise the following steps: (a) extracting PEth from a blood sample by contacting the blood sample with a solvent comprising one or more of chloroform and an alcohol having 1-4 carbon atoms to form a PEth extract; (b) concentrating the PEth extract to form a PEth concentrate; (c) derivatizing the PEth in the PEth concentrate with a derivatizing agent to form a single PEth derivative having a structure of formula (I):

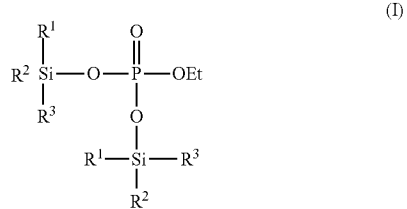

wherein each $R^1$, each $R^2$, and each $R^3$ independently is $C_{1-4}$alkyl; and (d) quantifying the amount of PEth derivative in the concentrate via GC-MS.

The blood sample can include intact PEth, decomposed PEth, or both. "Intact PEth" refers to a phospholipid form having a structure:

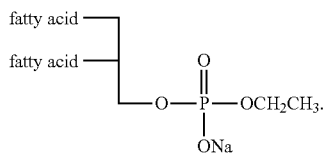

While the sodium salt is shown, the PEth can be present as the free acid or as a different acid salt. "Decomposed PEth" refers to PEth that has been chemically altered over time through, e.g., oxidation or hydrolysis, such as olefin oxidation, fatty acid hydrolysis, and/or glyceryl residue hydrolysis. The blood sample can be prepared by any method known to one skilled in the art. In some embodiments, the blood sample is a whole blood sample, which refers to a blood sample in liquid form. In various embodiments, a whole blood sample can be prepared by obtaining a blood sample from a subject (e.g., living or postmortem) and blotting the blood sample onto a filter paper or spot card. In some cases, the blood sample is a dried blood sample. In some embodiments, the blood sample is a dried blood sample. The dried blood sample can be prepared by obtaining a blood sample from a subject (e.g., living or postmortem), blotting the blood sample onto a filter paper or spot card, and then drying the blood sample (e.g., by air). The Examples section, below, provides additional details on preparation of the blood samples. In other embodiments, the blood sample can comprise whole blood.

Extracting the Sample

The methods disclosed herein involve extracting PEth from a blood sample (whole blood or dried blood) with a solvent comprising one or more of chloroform and an alcohol having 1-4 carbon atoms to form a PEth extract.

A suitable solvent allows solvation and breakdown of the matrix (e.g., filter paper or spot card) on which the blood spot is blotted (with or without drying), has a reasonable evaporation rate in the concentrating step, and minimizes or eliminates extraction of undesired components in the blood sample, such as urea and/or components that co-elute with the PEth derivative in the gas chromatography step. In various embodiments, the solvent comprises chloroform and alcohol in a ratio of 0:100 to 100:0 by volume. In some cases, the solvent comprises chloroform and alcohol in a ratio of about 90:10 to about 10:90 by volume (e.g., 90:10, 80:20, 70:30, 60:40, 50:50, 40:60, 30:70, 20:80, and 10:90 by volume). In various cases, the solvent comprises chloroform and alcohol in a ratio of about 90:10 to about 70:30 by volume. In some embodiments, the solvent comprises chloroform and alcohol in a ratio of about 80:20 or about 70:30 by volume.

The alcohol can include any alcohol having 1 to 4 carbon atoms. In some embodiments, the alcohol comprises one or more of methanol, ethanol, n-propanol, isopropyl alcohol, n-butanol, sec-butanol, isobutanol, and tert-butanol. In various embodiments, the alcohol comprises methanol and/or isopropyl alcohol. In some cases, the alcohol comprises methanol. In various cases, the alcohol comprises isopropyl alcohol. Suitable solvents can include, for example, chloroform and methanol or isopropyl alcohol, in a ratio of about 90:10, about 80:20, or about 70:30 by volume. In some cases, the solvent comprises chloroform and methanol in a ratio of about 70:30 by volume. In various cases, the solvent comprises chloroform and isopropyl alcohol in a ratio of about 80:20 by volume.

In some embodiments, the extraction step optionally involves mixing and/or sonicating the blood sample (whole blood or dried blood) with the solvent. Mixing can be continuous or intermittent, and can occur via any method known to those skilled in the art (e.g., manual, stirring, shaker). Mixing can occur at any temperature at which the sample does not decompose and the solvent does not evaporate, such as about 10 to 60° C. In some embodiments, mixing occurs at a temperature between about 15 to 35° C., such as about 25° C. Mixing can occur for any suitable time period, such as from about 1 to 120 min (e.g., 10, 15, 20, 25, 30, 35, 40, 45, 50, 55, 60, 80, 100, or 120 min). In some embodiments, mixing occurs from about 30 to 90 minutes, such as for about 60 minutes.

Sonication can occur continuously or intermittently. In some embodiments, sonication occurs continuously. Sonication can be carried out at any suitable temperature, such as in a range of about 0° C. to about 60° C. (e.g., 0, 5, 10, 15, 20, 25, 30, 35, 40, 45, 50, 55 or 60° C.). In some embodiments, sonication can take place at a temperature of about 22-25° C. Sonication can be carried out for a desired length of time, depending on the composition, composition size, and amount of energy to be delivered. For example, sonication can occur for a time period in the range of about 1 second to about 60 minutes, or about 5 seconds to about 30 minutes. In some cases, sonication can occur for a time period in the range of about 5 minutes to about 20 minutes (e.g., 5, 10, 15, or 20 minutes). In various cases, sonication can occur for a time period in the range of about 10 minutes to about 15 minutes, such as for 15 minutes.

In some embodiments, the method can further comprise washing the PEth extract with an aqueous solution. Washing the PEth extract with an aqueous solution can remove water soluble impurities that might otherwise complicate or interfere with the analysis of PEth. The aqueous solution can be neutral, acidic, or basic. Washing the extract can occur by any method known to one skilled in the art. In some embodiments, the aqueous the PEth extract is washed with an equal volume of aqueous solution to form an aqueous layer and an organic layer, and the aqueous layer is discarded.

Concentrating the PEth Extract

The PEth extract can be concentrated by any method known to one skilled in the art. In some embodiments, the concentration step includes heating the PEth extract. The PEth extract can be heated to any suitable temperature. In some cases, the PEth extract is heated to a temperature in a range of about 30 to 60° C. (e.g., 30, 35, 40, 45, 50, 55, or 60° C.). In some cases, the PEth extract is heated to a temperature in a range of about 35 to 45° C. In some cases, the PEth extract is heated at about 40° C. In some embodiments, the concentration step includes streaming gas through the PEth extract, which can decrease the time required to concentrate the PEth extract. The gas can comprise any suitable gas, such as compressed air or an inert gas (e.g., helium, argon, or nitrogen).

In some embodiments, the PEth extract is concentrated using a heating device comprising an evaporator and an aluminum block. In some cases, the heating device includes a dry bath (e.g., Corning LSE model 6785) equipped with at least one aluminum heating block (e.g., two aluminum heating blocks) containing a pattern of holes (e.g., a 4×5 pattern of 12 mm holes) and an evaporation system. The evaporation system can include a manifold capable of evaporating solvent from at least one PEth extract sample, such as two, three, four, five, six, or more samples. Each manifold outlet port can include a swivel adapter to direct the gas stream in a downward direction. The swivel adapter can be connected to a national pipe thread ("NPT") adapter that can terminate in a luer lock fitting. Dispensing needles (e.g., 4", 16-gauge needles) can be connected to each NPT adapter by luer lock. Such a configuration can allow a narrow gas stream to be directed into various different sample vials (e.g., test tubes, vials, vessels). In some cases, the threaded connections of the evaporation system include one quarter inch NPT. The back of the manifold can be connected to a gas supply through a regulator via tubing. The tubing can be fitted to the back of the manifold via a barbed hose adaptor. The regulator can be used to control gas flow. In some embodiments, the manifold setup can be mounted on a ring stand using a clamp, which allows for facile vertical repositioning to accommodate varying solution depths and evaporation vessel types. An example evaporation system is shown in FIG. 1.

An internal standard can be added to the PEth extract before concentration. In some embodiments, the internal standard comprises one or more of a phosphatidyl alcohol (e.g., phosphatidylmethanol ("PMeth") and phosphatidylbutanol ("PBut")), a deuterated phosphatidyl alcohol (e.g., PEth 16:0/18:1, in which one or both of the fatty acid residues are per-deuterated, or in which the ethyl head group is per-deuterated, such as PEth-d5)), and a long chain fatty acid. In various embodiments, the internal standard comprises PMeth, PBut, PEth-d5, or combinations thereof. In some embodiments, the PMeth and PBut are added to the PEth concentrate in an amount of about 0.1 to 0.5 µg/mL, such as about 0.25 µg/mL each of PMeth and PBut. In some embodiments, the PMeth and PBut are added to the PEth concentrate in an amount of about 1.0 to 3.0 µg/mL, such as about 2.0 µg/mL each of PMeth and PBut. In various cases, the internal standard comprises PEth-d5. The PEth-d5 can be added to the PEth concentrate in an amount of about 0.1 to 0.5 µg/mL, such as 0.25 µg/mL. In some cases, the PEth-d5 can be added to the PEth concentrate in an amount of about 1.0 to 3.0 µg/mL, such as 2.0 µg/mL.

Derivatizing the PEth Concentrate

The methods disclosed herein comprise derivatizing the PEth in the PEth concentrate with a derivatizing agent to form a single PEth derivative, an example of which is shown below:

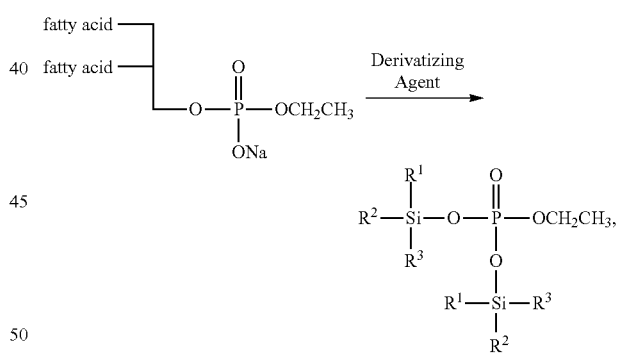

wherein each $R^1$, each $R^2$, and each $R^3$ independently is $C_{1-4}$alkyl. While the sodium salt is shown, the PEth can be present as the free acid or as a different acid salt. Derivatizing the PEth concentrate prevents thermal decomposition of the PEth when it is exposed to the high temperatures required for GC-MS analysis.

In some embodiments, $R^1$, each $R^2$, and each $R^3$ independently is methyl, ethyl, iso-propyl, n-butyl, sec-butyl, or tert-butyl. In some embodiments, each $R^1$, each $R^2$, and each $R^3$ independently is methyl or tert-butyl. In some cases, each $R^1$, $R^2$, and $R^3$ is methyl. In some cases, each $R^1$ and $R^2$ is methyl and each $R^3$ is tert-butyl. In some embodiments, the single PEth derivative is selected from the group consisting of:

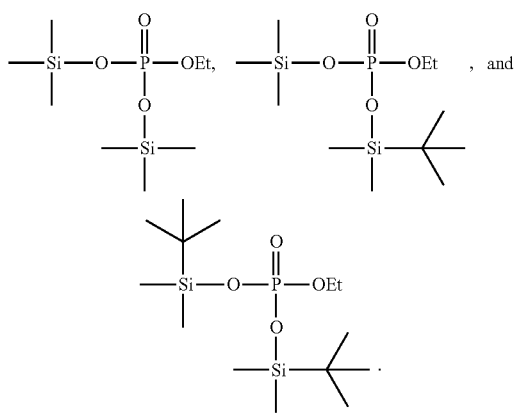

In some cases, the single PEth derivative is

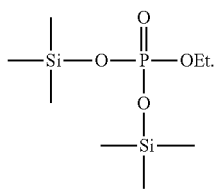

In various cases, the single PEth derivative is

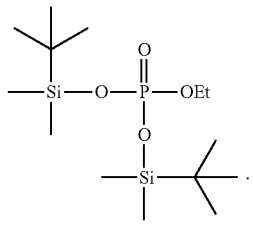 [SMILES: CCOP(=O)(O[Si](C)(C)C(C)(C)C)O[Si](C)(C)C(C)(C)C]

The derivatizing agent can be any agent suitable for derivatizing PEth for analysis by GC-MS, such as an acylating agent or a silylating agent. In some embodiments, the derivatizing agent comprises one or more silylating agents. In some embodiments, the silylating agent comprises one or more of N,O-Bis(trimethylsilyl)trifluoroacetamide ("BSTFA"), trimethylchlorosilane ("TMCS"), N-tert-Butyldimethylsilyl-N-methyltrifluoroacetamide ("MTBSTFA"), tert-Butyldimethylchlorosilane ("MTBCS"), N,O-Bis(trimethylsilyl)acetamide ("BSA"), Hexamethyldisilazane ("HMDS"), N-t-Butyldimethylsilylimidazole ("TBDMSIM"), N-Trimethylsilylimidazole ("TMSI"), N-Methyl-N-(trimethylsilyl)acetamide ("MSA"), N-(trimethylsilyl)dimethylamine ("TMSDMA"), N-trimethylsilyl-N-methyl trifluoroacetamide ("MSTFA"), and N,N-Diethyltrimethylsilylamine ("TMSDEA"). In various embodiments, the derivatizing agent comprises a mixture of BSTFA and TMCS or a mixture of MTBSTFA and MTBCS. In some cases, the derivatizing agent comprises a mixture of BSTFA and TMCS. In various cases, the derivatizing agent comprises a mixture of MSTDA and TMCS. In some embodiments, the derivatizing agent comprises MSTFA. In some embodiments, the mixture of BSTFA and TMCS is present in a ratio range of about 90:10 to 99.9:0.1 by volume. In various cases, the mixture of BSTFA and TMCS is present in a ratio of about 99:1 by volume.

The PEth can be derivatized in any suitable solvent. In some cases, the solvent comprises one or more of chloroform, acetonitrile, methylene chloride, toluene and xylene. In some embodiments, the solvent is chloroform. Derivatization of the PEth concentrate can occur at any suitable temperature. In various cases, the derivatization occurs at a temperature in a range of about 20 to 60° C. (e.g., 20, 25, 30, 35, 40, 45, 50, 55, or 60° C.). In some embodiments, the derivatization occurs at a temperature in a range of about 40 to 60° C. or about 35 to 45° C. In various cases, the derivatization occurs at about 40° C. In some embodiments, the reaction time for derivatization is about 10 to 100 minutes (e.g., 10, 15, 20, 25, 30, 35, 40, 45, 50, 55, 60, 65, 70, 75, 80, 85, 90, 95, or 100 minutes). In some cases, the reaction time is about 20 to 60 minutes. In some embodiments, the reaction time is about 45 minutes.

The methods described herein can include filtering the PEth derivative prior to subjecting it to GC-MS. Filtering the PEth derivative minimizes interfering peaks in the GC-MS chromatograph, improves peak shape, and provides improved detector response during GC-MS analysis. The PEth derivative can be filtered by any suitable method known to one skilled in the art. In some embodiments, the PEth derivative is filtered using a column, self-filtering vials, solid phase extraction and/or microextraction cartridges, or centrifugation followed by extraction. In various cases, the PEth derivative is filtered through a column comprising one or more filtering agents, such as silica gel and/or alumina. In various embodiments, the PEth derivative is filtered under positive pressure (e.g., at least 1.1 atm). For example, the PEth derivative can be pushed through a syringe comprising a filtering agent, such as silica gel and/or alumina.

Quantifying the PEth Derivative

The methods disclosed herein comprise quantifying the amount of PEth derivative in the concentrate via GC-MS.

The PEth derivative can be quantified using one or more gas chromatography methods and one or more mass spectrometry methods. In some embodiments, the PEth derivative is quantified using gas chromatography mass spectrometry ("GC-MS"), gas chromatography mass selective detector ("GC-MSD"), gas chromatography tandem mass spectrometry ("GC-MS/MS"), or gas chromatography mass spectrometry and flame ionization detector ("GC-MS/FID"). In various cases, the PEth derivative is quantified using GC-MS.

Any suitable ionization method can be used for the mass spectrometry described herein, such as electron impact ("EI"), fast atom bombardment ("FAB"), electrospray ionization ("ESI"), and atmospheric pressure chemical ionization ("APCI"). In some cases, the ionization method is EI.

The GC column used for quantifying the PEth derivative can be any suitable GC column, ranging from nonpolar to mid-polarity, such as a nonpolar phase column, a low-polarity phase column, or a mid-polarity phase column. In some embodiments, the column can comprise dimethylpolysiloxane, diphenyl, 1,4-bis(dimethylsiloxy)phenylene dimethylpolysiloxane, or a combination thereof. Suitable columns can include a nonpolar 100% dimethylpolysiloxane column (e.g., Agilent J&W HP-1 column), a low-polar 5%-diphenyl-95%-dimethylpolysiloxane column (e.g., Agilent J&W HP-5 column), a low-polar 1,4-bis(dimethylsiloxy)phenylene dimethylpolysiloxane (e.g., Rxi-5SiI MS column) and a mid-polar 50%-diphenyl-50%-dimethylpolysiloxane column (e.g., Agilent J&W HP-17 column). In some embodiments, the GC column is a low-polar column (e.g., 5%-diphenyl-95%-dimethylpolysiloxane column). In some embodiments, the column can further comprise an unphased guard column, i.e. a retention gap.

In some embodiments, the injector is in split mode. For example, the split can be constant (not pulsed) (e.g., up to 20:1). In various embodiments, the injector is in splitless mode. In some cases, injector can be in non-pulsed splitless mode with a purge time ranging range from 0.5 to 1.5 minutes (e.g., 0.75 minutes)

The GC-MS inlet can comprise any liner and any packing material that allows for quantification of the PEth derivative described herein. In some embodiments, the inlet liner can include a straight, single-tapered, double-tapered, or cyclo-configuration. In various embodiments, the packing material comprises silanized glass wool. The inlet temperature can be any temperature at which the PEth derivative is stable to decomposition. In some embodiments, the inlet temperature is in a range of about 100 to about 280° C. In various embodiments, the inlet temperature is about 275° C.

The PEth derivative can be prepared for GC-MS analysis by any method known to one skilled in the art. In some embodiments, the concentrated PEth derivative can be dissolved in a suitable solvent (e.g., chloroform). In various embodiments, the resulting PEth derivative sample has a PEth concentration of about 0.100 ng/µL to about 6.00 ng/µL. In some cases, the concentration of PEth in the sample is about 0.133 ng/µL to about 5.33 ng/µL.

The PEth derivative sample can be flowed through the GC-MS instrument at a temperature in a range of about 60 to 320° C. In some embodiments, the PEth sample is flowed through the GC-MS instrument using a temperature gradient. The temperature gradient can include an initial temperature ranging from about 55° C. to about 75° C., or from about 55° C. to about 100° C., and a final temperature of about 260° C. to about 350° C., with a ramp of about 3° C. per minute to about 50° C. per minute. In some embodiments, the initial and/or final temperature is held for a period of time (e.g., 1 to 10 minutes, 2 to 7 minutes, 3 minutes, 4 minutes, or 5 minutes). In some cases, the temperature gradient comprises two different ramping conditions, one at a lower temperature (e.g., about 3 to 7° C. per minute) and one at a higher temperature (e.g., about 30 to 50° C.), separated by an interim temperature of about 125 to about 175° C. (e.g., 150° C.). In various cases, the temperature gradient comprises an initial temperature of the about 60° C. and a final temperature of about 320° C., with a ramp of 5° C. per minute. In various embodiments, the temperature gradient comprises an initial temperature of the about 70° C. held for 3 minutes, which is ramped to 150° C. at 5° C. per minute, followed by a 40° C. per minute ramp to 280° C. that is held for 5 minutes.

The flow rate of the PEth derivative sample through the column depends on the size of the column. In some cases, a wider column requires a faster flow. The PEth derivative sample can be flowed through the GC-MS at a flow rate of about 1.0 to 2.0 mL per minute (e.g., with a 0.250 mm ID column). In some embodiments, the PEth sample is flowed through the GC-MS at a flow rate of about 1.6 mL per minute (e.g., with a 0.250 mm ID column).

Figure 2:
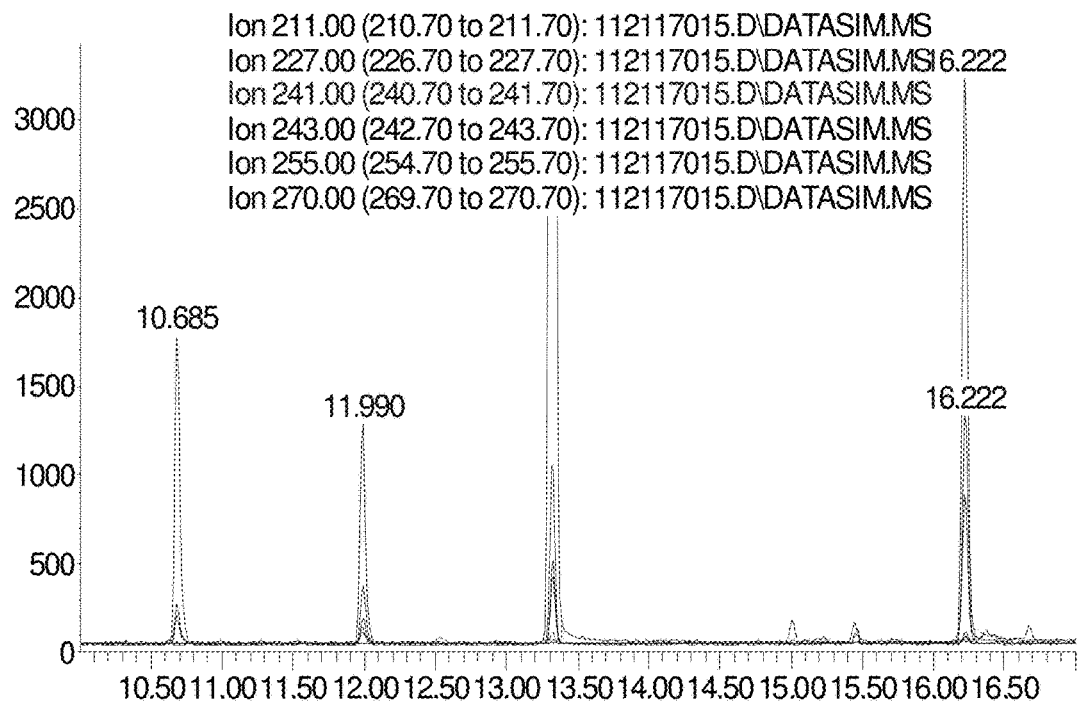
FIG. 2 depicts a GC-MS-SIM chromatogram of human negative blood extract from a dried blood spot displaying di-TMS alkyl-phosphate derivatives of PMeth (10.685 min.), PEth (11.990 min), and PBut (16.222 min).
Figure 4:
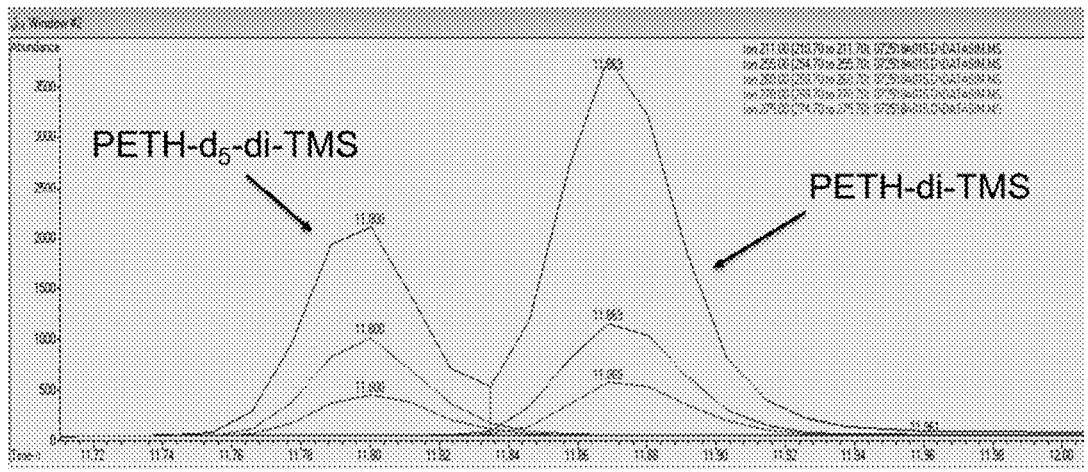
FIG. 4 depicts a gas-chromotography-mass-spectrometry-selective-ion-monitoring ("GC-MS-SIM") chromatogram displaying di-TMS alkyl-phosphate derivatives of PEth-d5 (11.800 min), and PEth (11.869 min).

In some embodiments, 0.133 ng/µL to 5.330 ng/µL of the PEth derivative sample is injected via splitless mode into an inlet lined with a single tapered liner and comprising silanized glass wool packing material at a temperature of 275° C. The PEth is flowed through a Rtx-5 ms, 30 m long×0.250 mm ID×0.250 mcm load column using an initial temperature of 70° C. held for 3 minutes, ramped up to 150° C. at 5° C. per minute, followed by a 40° C. per minute ramp to 280° C. held for 5 minutes, using a helium flow rate of 1.6 mL per minute. In embodiments in which the foregoing parameters are used, the PEth derivative elutes with a retention time range of about 11.5 to 12.5 minutes, depending on column length and the specific instrument used for the analysis, with a total run time of about 27 minutes. Quantification of the PEth derivative is linear down to at least 0.200 µg/mL using a selected ion monitoring method. The ions monitored are m/z=270 (the molecular ion for PEth), m/z=255, m/z=243, m/z=241 (internal standard ion of PMeth), m/z=227 (the base ion for PMeth), m/z=211 (base ion used for quantification of PEth and internal standard ion of PBut), and m/z=133, as shown in FIG. 2. In various embodiments, the ions monitored are m/z=275 (the molecular ion for PEth-d5), m/z=270 (the molecular ion for PEth), m/z=260, m/z=255, m/z=211 (base ion for PEth and PEth-d5), as shown in FIG. 4.

Examples

The following examples are provided for illustration and are not intended to limit the scope of the invention.

Materials and Methods

Agilent GC-MSD model 7890A/5975C fitted with a Restek Rtx-5 ms GC column (30 m×0.250 mm ID×0.250 mcm load); PMeth, PEth, and PBut from Avanti Polar Lipids; PEth-d5 from Eschelon Bioscience; $CHCl_3$ and IPA from EMD Millipore; BSTFA/TMCS from Alfa Aesar, silanized glass wool from Cresent Chemicals, 1 mL disposable syringes from Sigma Aldrich, general laboratory grade cotton, GE Healthcare-Whatman syringe filters, silica gel from EM Science, laboratory-grade sand prepared from washed common sand, and DBS cards comprised of Whatman 903 grade paper.

Preparation and Extraction of PEth from a Whole Blood Sample

Whole blood (40 µL, from living or postmortem samples) was placed in an extraction vessel containing about 1.0 to 1.5 mL of $CHCl_3$/IPA and about 0.25 µg/mL each of PMeth or PBut, or 0.25 µg/mL of PEth-d5. Alternatively, whole blood (40 µL, from living or postmortem samples) was placed in an extraction vessel containing about 1.0 to 1.5 mL of $CHCl_3$/IPA and about 2.0 µg/mL each of PMeth or PBut, or 2.0 µg/mL of PEth-d5

Preparation and Extraction of PEth from a Dried Blood Sample

Whole blood (40 µL, from living or postmortem samples) was spotted onto a dried blood spot card via an Eppendorf-type pipette in two 20 µL aliquots and air dried. The entire dried blood spot card was cut using a single hole-puncher, and the resulting disk was placed in an extraction vessel containing about 1.0 to 1.5 mL of $CHCl_3$/IPA and about 0.25 µg/mL each of PMeth and PBut, or 0.25 µg/mL or PEth-d5. Alternatively, the entire dried blood spot card was cut using a single hole-puncher, and the resulting disk was placed in an extraction vessel containing about 1.0 to 1.5 mL of $CHCl_3$/IPA and about 2.0 µg/mL each of PMeth and PBut, or 2.0 µg/mL or PEth-d5. The extraction vessel was then sonicated continuously for 15 minutes at 22 to 25° C.

Washing of the PEth Extract

The initial PEth extract was washed with an equal volume of water (neutral, acidic, or basic) and this aqueous layer was discarded. The remaining organic extract was transferred to a clean vessel such as a GC autosampler vial.

Concentration of PEth from a PEth Extract

The solvent was removed from extraction vessel by pipet and placed in a GC autosampler vial. The vial was then placed in an aluminum heating block set, as described in the Concentrating the Extract Section, above, and in FIG. 1, at 40° C. and evaporated under a dry air stream to visible dryness.

Derivatization of the PEth Concentrate

The PEth concentrate was reconstituted in 100 to 200 µL of CHCl₃ and 12.5 to 200 µL of BSTFA/TMCS. The vial was then capped with a crimp top, vortexed, and heated to about 40° C. for about 45 minutes.

Filtration of the PEth Derivative

The PEth derivative was evaporated to visible dryness, reconstituted in 200 µL of CHCl₃, and filtered via a filtering assembly. The filtering assembly included a syringe filter attached to a syringe containing a cotton plug and a column of silica gel/alumina topped with a layer of sand of approximately 20 mesh particle size. The filtrate was then concentrated to dryness and reconstituted in 30 µL of chloroform for analysis by GC-MS.

Figure 3A:
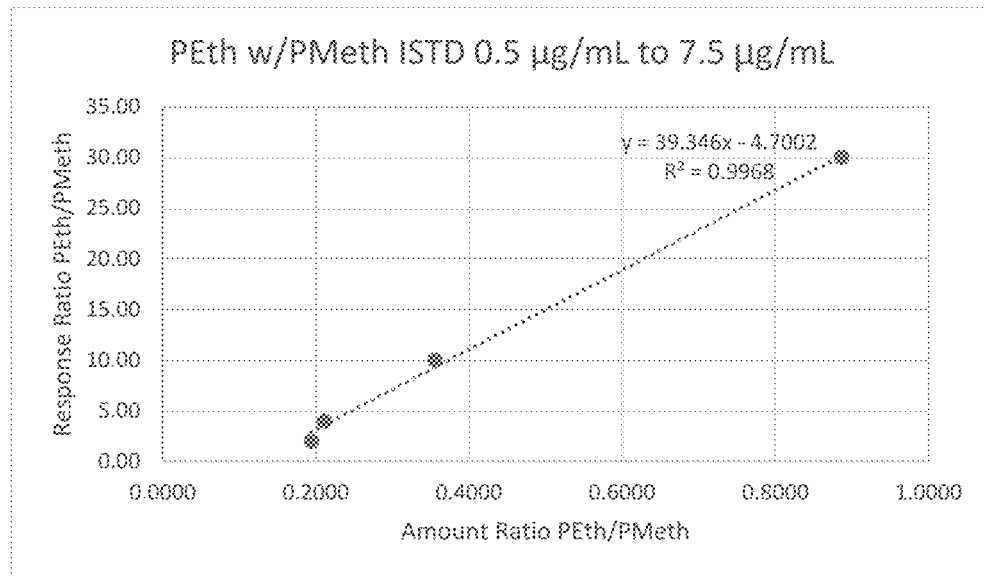
FIG. 3A depicts a calibration curve of PEth with PMeth, resulting from the conditions described in the Quantification of the PEth Derivative by GC-MS section of the Examples.
Figure 3B:
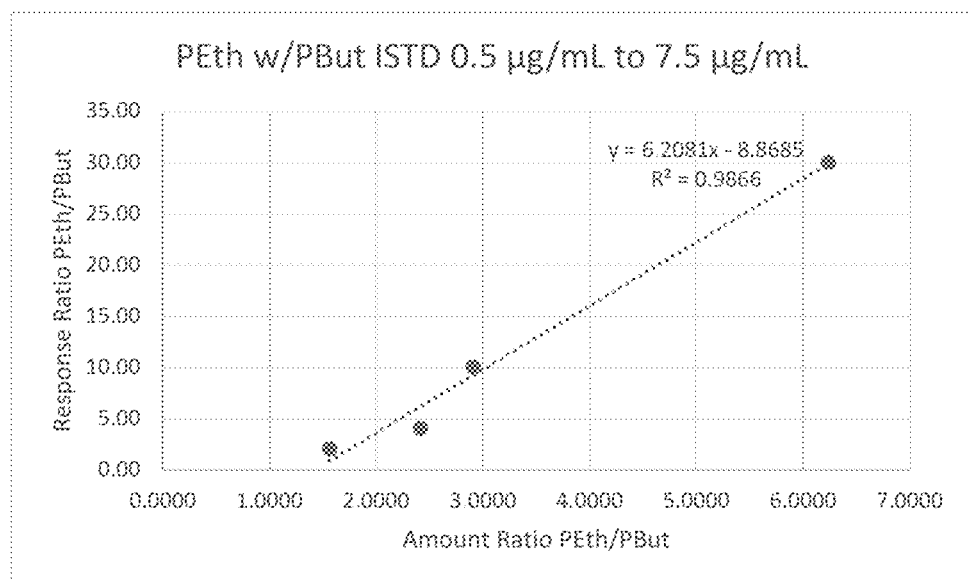
FIG. 3B depicts a calibration curve of PEth with PBut, resulting from the conditions described in the Quantification of the PEth Derivative by GC-MS section of the Examples.

Quantification of the PEth Derivative by GC-MS Using PMet and PBut Internal Standards Data analysis was performed using a RTE integrator to generate a calibration curve of at least four points using qualifying ion ratios of +/−20%. The peaks of interest were visualized in a time window of 10 to 17 minutes, extracted from the SIM data file, and integrated. A linear calibration curve was generated from a plot of the integration ratios of selected analytes as a function of concentration. See the integration table, below, and the calibration curves in FIGS. 3A and 3B.

| | m/z 211 SIM (RTE integrator) | | | | |
|---|---|---|---|---|---|
| PEth, µg/mL | RT 11.9 min | RT 10.7 min PMet (IS) | RT 16.2 min PBut (IS) | y | x |
| 0.5 | 5187 | 26726 | 3317 | 0.1941 | 2.00 |
| 1.0 | 9999 | 47311 | 4138 | 0.2113 | 4.00 |
| 2.5 | 11624 | 32740 | 3998 | 0.3550 | 10.00 |
| 7.5 | 23242 | 26218 | 3727 | 0.8865 | 30.00 |

GC-MS Protocol:

On an Agilent 7890A/5975C GC-MSD, 1.04 of solution is injected onto a Rtx-5 ms GC column (30 m long×0.250 mm ID×0.250 mcm load), inlet temperature of 275° C. in splitless mode, operated at a constant helium carrier gas flow rate of 1.6 mL/min (alternatively, hydrogen or nitrogen can be used as the carrier gas), with an oven temperature profile of 70° C. initial temperature held at 3 minutes and ramped at 5° C. per minute to 150° C., followed by a 40° C. per minute ramp to 280° C. and held at 280° C. for 5 minutes, analyzed in SIM mode (m/z=270, 255, 243, 241, 227, 211, 133).

Quantification of the PEth Derivative by GC-MS Using PEth-d5 Internal Standard

Figure 5A:
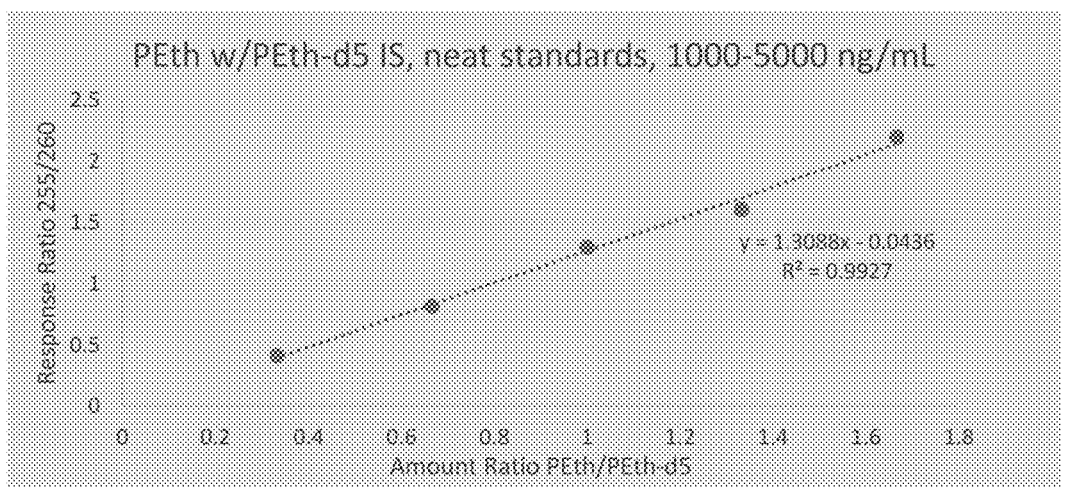
FIG. 5A depicts a calibration curve of di-TMS alkyl-phosphate derivatives of PEth-d5 and PEth in neat standards by methods described herein.
Figure 5B:
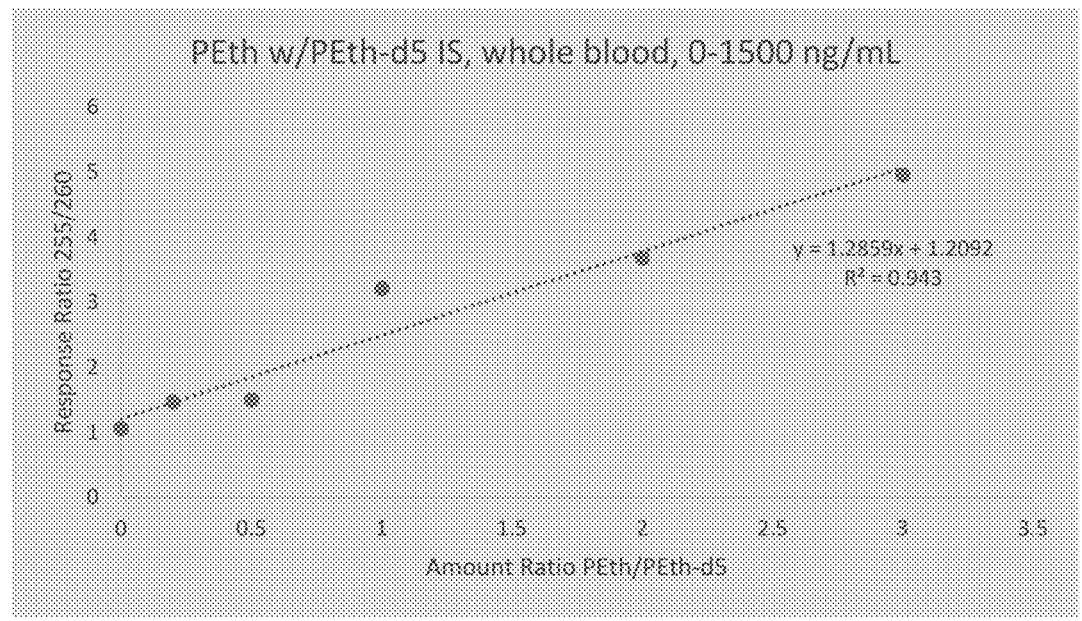
FIG. 5B depicts a calibration curve of di-TMS alkylphosphate derivatives of PEth-d5 and PEth in whole blood standards by methods described herein.
Figure 5C:
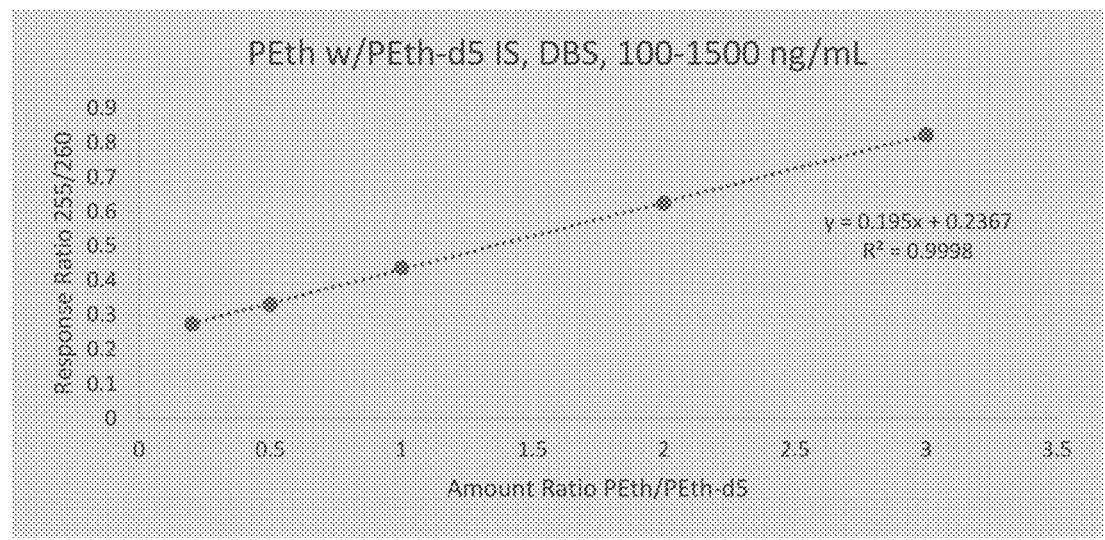
FIG. 5C depicts a calibration curve of di-TMS alkylphosphate derivatives of PEth-d5 and PEth in dried blood standards by methods described herein.

Data analysis was performed using a RTE integrator to generate a calibration curve of at least four points using qualifying ion ratios of +/−20%. The peaks of interest were visualized in a time window of 10 to 17 minutes, extracted from the SIM data file, and integrated. A linear calibration curve was generated from a plot of the integration ratios of selected analytes as a function of concentration. See the integration table, below, and the calibration curves in FIGS. 5A, 5B, and 5C.

Internal Standards

| PEth, ng/mL | m/z = 255 | PEth-d5 (ng/mL) | m/z = 260 | x | y |
|---|---|---|---|---|---|
| 1000 | 659 | 3000 | 1602 | 0.333333 | 0.411361 |
| 2000 | 1673 | 3000 | 2053 | 0.666667 | 0.814905 |
| 3000 | 3020 | 3000 | 2330 | 1 | 1.296137 |
| 4000 | 5109 | 3000 | 3180 | 1.333333 | 1.606604 |
| 5000 | 6294 | 3000 | 2865 | 1.666667 | 2.196859 |

Whole Blood

| PEth, ng/mL | m/z = 255 | PEth-d5 (ng/mL) | m/z = 260 | x | y |
|---|---|---|---|---|---|
| 0 | 349 | 500 | 330 | 0 | 1.057576 |
| 100 | 419 | 500 | 285 | 0.2 | 1.470175 |
| 250 | 459 | 500 | 306 | 0.5 | 1.5 |
| 500 | 1287 | 500 | 401 | 1 | 3.209476 |
| 1000 | 1228 | 500 | 334 | 2 | 3.676647 |
| 1500 | 1720 | 500 | 347 | 3 | 4.956772 |

Dried Blood

| PEth, ng/mL | m/z = 255 | PEth-d5 (ng/mL) | m/z = 260 | x | y |
|---|---|---|---|---|---|
| 100 | 71 | 500 | 258 | 0.2 | 0.275194 |
| 250 | 68 | 500 | 205 | 0.5 | 0.331707 |
| 500 | 104 | 500 | 238 | 1 | 0.436975 |
| 1000 | 138 | 500 | 221 | 2 | 0.624434 |
| 1500 | 185 | 500 | 225 | 3 | 0.822222 |

GC-MS Protocol:

On an Agilent 7890A/5975C GC-MSD, 1.04 of solution was injected onto a Rtx-5 ms GC column (30 m long×0.250 mm ID×0.250 mcm load), inlet temperature of 275° C. in splitless mode, operated at a constant helium carrier gas flow rate of 1.6 mL/min (alternatively, hydrogen or nitrogen can serve as the carrier gas), with an oven temperature profile of 70° C. initial temperature held at 3 minutes and ramped at 5° C. per minute to 150° C., followed by a 40° C. per minute ramp to 280° C. and held at 280° C. for 5 minutes, analyzed in SIM mode (m/z=275, 270, 260, 255, 211).

The foregoing description is given for clearness of understanding only, and no unnecessary limitations should be understood therefrom, as modifications within the scope of the invention may be apparent to those having ordinary skill in the art. For example, alternative means of quantitation may apply including, but not limited to, a single point internal standard method, a single point external standard method, a multi-point external standard method, or a standard addition method.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

The use of the terms "a," "an," "the," and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise indicated. No language in the specification should be construed as indicating any non-claimed element as essential to the practice of the invention.

As used herein, the terms "about" and "approximately" generally mean plus or minus 10% of the stated value. For example, about 0.5 would include 0.45 and 0.55, about 10 would include 9 to 11, about 1000 would include 900 to 1100.

When specific numbers are recited herein, they implicitly include the stated value plus or minus 10% of the stated value. For example, about 0.5 would include 0.45 and 0.55, about 10 would include 9 to 11, about 1000 would include 900 to 1100.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed:

1. A method for quantifying phosphatidylethanol ("PEth") in a blood sample comprising:
   (a) extracting PEth from the blood sample by contacting the blood sample with a solvent comprising one or more of chloroform and an alcohol having 1-4 carbon atoms to form a PEth extract;
   (b) concentrating the PEth extract to form a PEth concentrate;
   (c) derivatizing the PEth in the PEth concentrate with a derivatizing agent to form a single PEth derivative having a structure of formula (I):

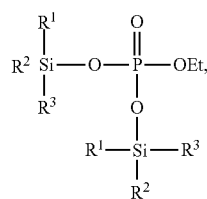

wherein each $R^1$, each $R^2$, and each $R^3$ independently is $C_{1-4}$alkyl; and
   (d) quantifying the amount PEth derivative in the concentrate by gas chromatography mass spectrometry ("GC-MS").

2. The method of claim 1 wherein the blood sample comprises intact PEth, decomposed PEth, or both.

3. The method of claim 1, wherein the blood sample is a dried blood sample.

4. The method of claim 1, wherein the blood sample is a whole blood sample.

5. The method of claim 1 wherein each $R^1$, each $R^2$, and each $R^3$ independently is methyl or tert-butyl.

6. The method of claim 5, wherein each $R^1$, $R^2$, and $R^3$ is methyl or each $R^1$ and $R^2$ is methyl and each $R^3$ is tert-butyl.

7. The method of claim 5, wherein the single PEth derivative is selected from the group consisting of:

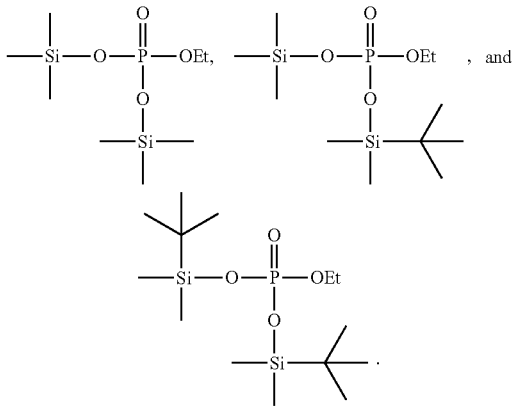

8. The method of claim 1, wherein the solvent comprises chloroform and alcohol in a ratio of 90:10 to 70:30 by volume.

9. The method of claim 1, wherein the alcohol comprises one or more of methanol, ethanol, n-propanol, isopropyl alcohol, n-butanol, sec-butanol, isobutanol, and tert-butanol.

10. The method of claim 1, wherein the extracting comprises mixing or sonicating the blood sample with the solvent, the concentrating comprises heating the extract, or both.

11. The method of claim 1, wherein the derivatizing occurs in a derivatizing solvent comprising one or more of chloroform, acetonitrile, methylene chloride, toluene, and xylene.

12. The method of claim 1, wherein the derivatizing agent is a silylating agent, optionally wherein the silylating agent comprises one or more of N,O-Bis(trimethylsilyl)trifluoroacetamide ("BSTFA"), trimethylchlorosilane ("TMCS"), N-tert-Butyldimethylsilyl-N-methyltrifluoroacetamide ("MTBSTFA"), tert-Butyldimethylchlorosilane ("MTBCS"), N,O-Bis(trimethylsilyl)acetamide ("BSA"), Hexamethyldisilazane ("HMDS"), N-t-Butyldimethylsilylimidazole ("TBDMSIM"), N-Trimethylsilylimidazole ("TMSI"), N-Methyl-N-(trimethylsilyl)acetamide ("MSA"), N-(trimethylsilyl)dimethylamine ("TMSDMA"), N-trimethylsilyl-N-methyl trifluoroacetamide("MSTFA"), and N,N-Diethyltrimethylsilylamine ("TMSDEA").

13. The method of claim 12, wherein the silylating agent comprises (i) a mixture of BSTFA and TMCS, (ii) a mixture of MTBSTFA and MTBCS, (iii) a mixture of MSTDA and TMCS, or (iv) MSTFA.

14. The method of claim 13, wherein the silylating agent comprises a mixture of BSTFA and TMCS in a ratio of 99:1 by volume.

15. The method of claim 1, further comprising washing the PEth extract and/or filtering the PEth concentrate optionally under positive pressure through silica gel or alumina.

16. The method of claim 1, further comprising adding an internal standard to the PEth concentrate, optionally wherein the internal standard comprises one or more of a phosphatidyl alcohol, a deuterated phosphatidyl alcohol, and a long chain fatty acid.

17. The method of claim 16, wherein the internal standard comprises phosphatidylmethanol ("PMeth"), phosphatidylbutanol ("PBut"), phosphatidylethanol-d5, or combinations thereof.

18. The method of claim 1, wherein the GC-MS comprises a nonpolar phase column, a low-polarity phase column, or a mid-polarity phase column.

19. The method of claim 18, wherein the column comprises dimethylpolysiloxane, diphenyl, 1,4-bis(dimethylsiloxy)phenylene dimethylpolysiloxane, or a combination thereof.

20. The method of claim 19, wherein the column comprises 100% dimethylpolysiloxane, 5%-diphenyl-95%-dimethylpolysiloxane, 50%-diphenyl-50%-dimethylpolysiloxane, 1,4-bis(dimethylsiloxy)phenylene dimethylpolysiloxane, or combinations thereof.

21. The method of claim 1, wherein the quantifying comprises:
(i) injecting about 0.100 ng/μL to about 6.00 ng/μL of the PEth derivative in chloroform into the GC-MS at an initial temperature of about 55 to about 100° C. held for about 1 to 10 minutes;
(ii) flowing the PEth derivative through the GC-MS at a rate of about 1.0 mL to about 2.0 mL per minute;
(iii) ramping the initial temperature to an interim temperature of about 125 to about 175° C. at a rate of about 3 to 7° C. per minute;
(iv) ramping the interim temperature to a final temperature of about 250 to about 350° C. at a rate of about 30 to 50° C. per minute.

22. The method of claim 21, wherein the quantifying comprises: (i) injecting about 0.133 ng/pL to 5.330 ng/pL of the PEth derivative in chloroform into the GC-MS at an initial temperature of about 70° C. held for about 3 minutes; (ii) flowing the PEth derivative through the GC-MS at a rate of about 1.6 mL per minute; (ii) ramping the initial temperature to an interim temperature of about 150° C. at a rate of about 5° C. per minute; (iv) ramping the interim temperature to a final temperature of about 280° C. at a rate of about 40° C. per minute; and (v) holding the final temperature for about 5 minutes.

* * * * *